United States Patent [19]

Helmstetter

[11] Patent Number: 4,465,978

[45] Date of Patent: Aug. 14, 1984

[54] SIGNAL CONDITIONING CIRCUIT

[75] Inventor: Paul M. Helmstetter, Littleton, Colo.

[73] Assignee: Biosound, Inc., Indianapolis, Ind.

[21] Appl. No.: 507,879

[22] Filed: Jun. 27, 1983

Related U.S. Application Data

[63] Continuation of Ser. No. 242,967, Mar. 12, 1981, abandoned.

[51] Int. Cl.³ .............................................. H03K 5/00
[52] U.S. Cl. .................................... 328/168; 307/264; 307/492; 307/493; 328/145; 328/171
[58] Field of Search ............... 307/264, 490, 491, 492, 307/493, 498; 328/145, 168, 171

[56] References Cited

U.S. PATENT DOCUMENTS 3,234,404 2/1966 Peters ................................... 328/145
3,502,959 3/1970 Stellman .............................. 328/145
4,002,977 1/1977 Sun et al. ............................. 328/145
4,233,564 11/1980 Kerbel ................................. 328/145

Primary Examiner—John Zazworsky
Attorney, Agent, or Firm—Woodard, Weikart, Emhardt & Naughton

[57] ABSTRACT

A signal conditioning circuit includes a logarithmic signal compression circuit for compressing wide dynamic range input signals to a dynamic range which is a predetermined portion of the dynamic range of an output utilization apparatus. There is provided, additionally, means for detecting the presence of the high level signals and superimposing a signal representative of the high level signals on the compressed signals to provide a combined output signal which, while compressed to the range of the output utilization apparatus, contains definable low level and high level signals from a wide dynamic range input signal.

9 Claims, 1 Drawing Figure

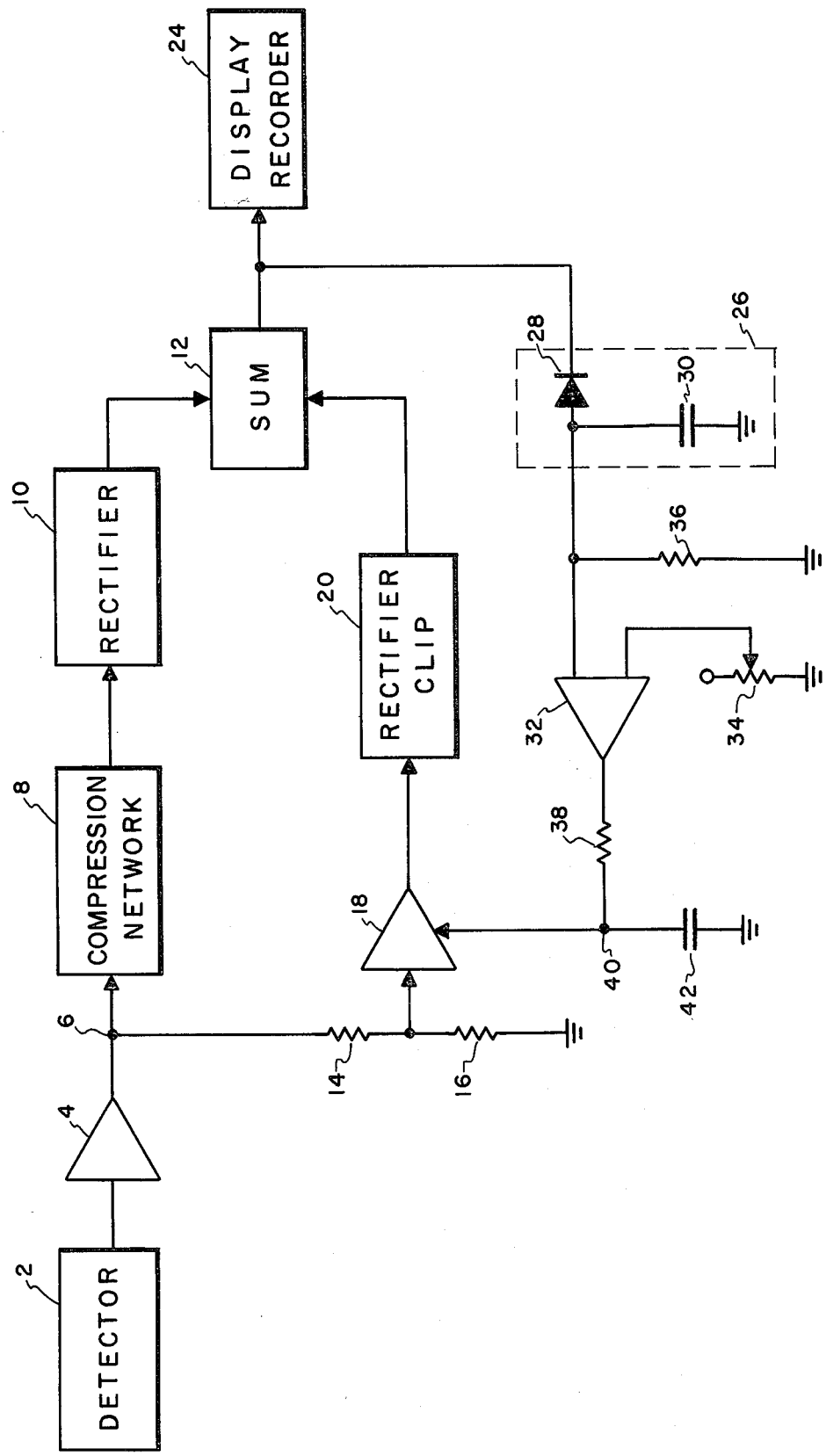

SIGNAL CONDITIONING CIRCUIT

This is a continuation of application Ser. No. 242,967, filed Mar. 12, 1981, now abandoned.

BACKGROUND OF THE INVENTION

The present invention relates to signal conditioning circuits. More particularly, it relates to characterizing signals to enhance the availability of the data content thereof.

In the art of data acquisition and utilization, it has been found that the acquired data has a wider dynamic range than can be accommodated by the utilization apparatus. One instance of such a system is seen in certain medical investigatory techniques. For example a technique for non-invasive examination of internal bodily organs is accomplished through the use of ultrasonic probes which transmit sonic pulses into the body and responds to echoes from tissue interfaces within the body. The echo signals detected by the transducer have a dynamic range that is significantly greater than can be accommodated by a cathode ray tube display device or by an associated hard copy recorder. In order that the low level signals may be raised to a useful level, the detected signals are amplified to the point necessary for the recognition of such low level signals. In such systems, it is usual to employ a compression system which may, in fact, involve a logarithmic compression amplifier which compresses the high level signals. In such systems, the high level signals are frequently merged into an indistinguishable blur. It has been found, however, that the medical practitioners utilizing such devices, are not only interested in a recognizable definition of the low level signals, but are also keenly interested in a sharp definition of the high level signals.

SUMMARY OF THE INVENTION

It is, accordingly, an object of the present invention to provide an improved signal conditioning circuit which obviates the shortcomings of previous circuits.

It is another object of the present invention to provide an improved signal conditioning circuit as set forth which effectively compresses the dynamic range of input signals while retaining definition of both high level and low level signals.

In accomplishing these and other objects, there has been provided, in accordance with the present invention, a signal conditioning circuit which includes a logarithmic signal compression circuit for compressing wide dynamic range input signals to a dynamic range which is a predetermined portion of the dynamic range of an output utilization apparatus. There is provided, additionally, means for detecting the presence of the high level signals and superimposing a signal representative of the high level signals on the compressed signals to provide a combined output signal which, while compressed to the range of the output utilization apparatus, contains definable low level and high level signals from a wide dynamic range input signal.

BRIEF DESCRIPTION OF THE DRAWINGS

A better understanding of the present invention may be had from the following detailed description when read in the light of the accompanying drawings, in which:

The single FIGURE is a block schematic diagram of a signal conditioning circuit embodying the present invention.

DETAILED DESCRIPTION

Referring now to the drawing in more detail, there is shown in the single FIGURE a signal conditioning circuit which may be used in such environment as medical diagnostic apparatus. A signal detector 2 which may be in the form of an ultrasonic transducer, has its output connected to a preamplifier 4. The output of the preamplifier 4 is connected to a junction 6. The junction 6 is connected, first to a compression network 8. The compression network may include a conventional logarithmic amplifier such as a integrated circuit chip identified as TL441C produced by Texas Instruments. The compression network 8 has a transfer characteristic such that the lower level signals are amplified while the higher level signals are compressed. The output of the compression network is applied to a rectifier 10, the output of which is, in turn, applied to a summing circuit 12.

The junction 6 is also connected to an attenuator comprising a first and a second serially connected resistor 14 and 16. The junction between the resistors 14 and 16 is connected to the input of a linear variable gain amplifier 18. The output of the amplifier 18 varies in linear fashion with the signal at junction 6 and is applied to the input of a rectifier/clipping circuit 20. The output of the circuit 20 is a signal which has not been compressed and which is connected to a second input of the summing network 12 where it is summed with the compressed signal at the first input. The output of the summing network 12 is connected to the input of an ultimate utilization device 24 which may be in the form of a CRT display or a hard copy recorder. The summing network 12 also has its output connected to a feedback network which includes, first, a peak detector 26. The peak detector includes a diode 28 and a capacitor 30. The output of the peak detector is connected to one input terminal of an error amplifier 32. The second input terminal of which is connected to a reference voltage source 34. An input resistor 36 is connected between the first mentioned input terminal of the amplifier 32 and ground. The output of the error amplifier 32 is coupled through a resistor 38 to a junction 40. A capacitor 42 is coupled between the junction 40 and ground. The junction 40 is also connected to the gain control input of the variable gain amplifier 18.

In operation, the signal from the detector or transducer 2 is amplified by the amplifier 4 to raise it to a suitable level overall. The output of the amplifier 4 is further amplified by the compression network 8. As previously noted, the compression network has a logarithmic transfer characteristic such that the lower amplitude signals are significantly amplified, in accordance with the steeper initial leg of the logarithmic curve. On the other hand, the higher level signals respond in accordance with the flatter portion of the transfer characteristic curve of the compression network 8 and are, accordingly, amplified to a much less degree. This, in turn, provides a large degree of compression of the higher level signals while amplifying the lower level signals to the level necessary to be of utility at the output device which, as noted, may be a CRT display device or a hard copy recorder or both.

Since the signals which may be used by the utilization device must be unidirectional, the output of the compression network 8 is rectified by the rectifier network 10 to provide such unidirectional signals. A key feature of the compression network 8 is that the dynamic range of the signals derived from the detector 2 are compressed to a dynamic range which is a predetermined portion of the dynamic range of the utilization device 24. Exemplary of such a compression is that the signals applied to the utilization or display device 24 from the compression network by way of the rectifier 10 and the summing unit 12 is about sixty percent of the maximum dynamic range of the display unit 24 itself.

The amplified output signals from the detector 2 are applied through the attenuator comprising the resistors 14 and 16 to the input of the variable gain amplifier 18. This output, in order to again provide the unidirectional signals previously mentioned, is rectified by the rectifier 20. Inasmuch as the low level signals receive the maximum amplification through the compression netowrk 8, the output of the amplifier 18 and rectifier 20 is clipped to remove the low level siganls from the output of the rectifier 20. This leaves signals representative of the higher level signals to be inserted into the summing unit 12 along with superimposed upon the rectified output of the compression network 8. Thus, the summation of the rectified output of the compression network 8 and the rectified and clipped output of the amplifier 18, when applied to the input of the utilization device represented by the display/recorder unit 24 comprise a signal designed to match the dynamic range of the utilization device 24 while maintaining a high order of definition of both the low level and the high level signals from the detector 2.

To assure that the composite signal has a dynamic range which is matched to that of the display/recorder 24, a feedback network is connected from the output of the summing unit 12 to control the gain of the variable gain amplifier 18 in accordance with the peak value of the composite signal. To this end, the feedback circuits includes the peak detector 26 comprised of the diode 28 and the capacitor 30. The output of the peak detector 26 is connected to one input terminal of a comparator or error amplifier 32, the other input terminal of which is connected to the source of reference voltage 34. The source of reference voltage 34 is adjusted to a value which is representative of the value of the peak signal which represents the maximum range of the display/recorder 24. That reference signal is compared with the actual peak value derived from the summing unit 12 and the peak detector 26. The result of that comparison is applied through the filter 30, comprised of the resistor 38 and the capacitor 42, to control the gain of the amplifier 18. Thus controlled, the composite signal from the summing junction will have peak values which match the maximum response characteristic of the utilization device 24.

Thus there has been provided, in accordance with the present invention, an improved signal conditioning circuit for coupling a wide dynamic range input signal source to a utilization device with a much narrower dynamic range by compressing the dynamic range of the input signals while yet retaining the desired definition of both the low level signals and the high level signals.

The embodiments of the invention in which an exclusive property or privilege is claimed are defined as follows:

1. A signal conditioning circuit for compressing a wide dynamic range input signal to a narrower range utilization apparatus while retaining the desired definition of both low and high level portions of said input signal, said circuit comprising:
   input means providing said input signal;
   a signal compression network having an input connected to said input means to receive said input signal, said compression network having an output which varies in a compressed fashion with said input signal and is of a dynamic range which is a predetermined portion of the dynamic range acceptable by said utilization apparatus;
   a non-compression network including a linear signal amplifier having an input also connected to said input means to receive said input signal and having an output which varies in a linear non-compressed fashion with said input signal;
   clipping means connected to the output of said linear signal amplifier to eliminate signals representative of low level portions of said input signal, said clipping means having an output which varies in a linear non-compressed fashion with the high level portions of said input signal, and
   summing means connected to said output of said compression network and said output of said clipping means to superimpose said output of said clipping means onto said output of said compression network to provide a composite output signal for application to said utilization apparatus.

2. A signal conditioning circuit as set forth in claim 1 wherein said signal compression network includes a logarithmic amplifier wherein low level portions of said input signal are significantly amplified while high level portions of said input signal are compressed.

3. A signal conditioning circuit as set forth in claim 2 wherein said dynamic range of said output of said logarithmic amplifier is limited to substantially sixty percent of said dynamic range acceptable by said utilization apparatus.

4. A signal conditioning circuit as set forth in claim 3 wherein rectifying means is connected between said logarithmic amplifier and said summing means.

5. A signal conditioning means as set forth in claim 4 wherein said clipping means includes rectifying means.

6. A signal conditioning means as set forth in claim 1 wherein said linear signal amplifier is a variable gain amplifier.

7. A signal conditioning circuit as set forth in claim 6 wherein feedback means are connected between said output of said summing means and a gain control input on said variable gain amplifier whereby to control the gain of said variable gain amplifier in response to the level of said composite signal.

8. A signal conditioning circuit as set forth in claim 7 wherein said feedback means includes peak detecting means whereby to control said gain of said variable gain amplifier in response to a peak value of said composite signal.

9. A signal conditioning circuit as set forth in claim 8 wherein said feedback means includes comparator means connected between said peak detecting means and said variable gain amplifier to compare said peak value of said composite signal with a reference signal to provide a gain control signal according to the resultant of the comparison.

* * * * *